United States Patent [19]

Schumann

[11] Patent Number: Plant 5,933

[45] Date of Patent: Apr. 7, 1987

[54] GERANIUM PLANT NAMED TANGO

[75] Inventor: Ingeborg Schumann, Bad Ems, Fed. Rep. of Germany

[73] Assignee: Fischer Geraniums, Inc., Netherlands Antilles

[21] Appl. No.: 761,014

[22] Filed: Jul. 31, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A geranium plant named Tango having red flower color; semi-double flower form with large flowerhead; dark green foliage; fast rooting; very good chlorophyll quality for transportation; small zonation; and good weather resistance.

1 Drawing Figure

The present invention comprises a new and distinct cultivar of geranium, botanically known as *Pelargonium zonale,* and hereinafter referred to by the cultivar name Tango.

Tango is a product of a planned breeding program which had the objective of creating new geranium cultivars having intense bright red flower color, semi-double flower form, large flowerhead, good chlorophyll quality for shipping, durability, and very fast rooting.

Tango was originated from a hybridization made by Ingeborg Schumann in a controlled breeding program in Hillscheid, Federal Republic of Germany in 1981. The female parent was an inbred line of Alex. The male parent of Tango was Bern of the "Pelfi" ® series of Pelargonien-Fischer KG, Hillscheid, Federal Republic of Germany. Both parents are unpatented.

Tango was discovered and selected as one flowering plant within the progeny of the stated cross by Ingeborg Schumann on June 4, 1982 in a controlled environment in Hillscheid, Federal Republic of Germany.

The first act of asexual reproduction of Tango was accomplished when vegetative cuttings were taken from the initial selection in January of 1983 in a controlled environment in Hillscheid, Federal Republic of Germany by a technician working under formulations established and supervised by Ingeborg Schumann. Horticultural examination of selected units initiated in the spring of 1983 and 1984 has demonstrated that the combination of characteristics as herein disclosed for Tango are firmly fixed and are retained through successive generations of asexual reproduction.

Tango has not been observed under all possible environmental conditions. The phenotype may vary significantly with variations in environment such as temperature, light intensity, and day length. The following observations, measurements and comparisons describe plants grown in Hillscheid, Federal Republic of Germany, under conditions which approximate those generally used in commercial practice.

The following traits have been repeatedly observed and are determined to be basic characteristics of Tango, which in combination distinguish this geranium as a new and distinct cultivar.

1. Intense red flower color.
2. Semi-double flower form with large flowerhead.
3. Dark green foliage.
4. Very good chlorophyll quality for transportation.
5. Very fast rooting.

6. Good weather resistance.
7. Very little zonation.

The accompanying photographic drawing shows typical flower and foliage characteristics of Tango, with colors being as true as possible with illustrations of this type.

In the following description color references are made to The Royal Horticultural Society Colour Chart. The color values were determined between 10:00 a.m. and 11:00 a.m. on May 22, 1985 under 35,000 Lux light intensity at Hillscheid, Federal Republic of Germany.

CLASSIFICATION

*Botanical.*—A hybrid of the genus *Pelargonium l'hert* and species *Pelargonium zonale.*

*Commercial.*—Tango.

INFLORESCENCE

A. Umbel:
- *Average diameter.*—119 mm.
- *Average depth.*—57 mm.
- *Penduncle length.*—176 mm.
- *Pedicel length.*—28 mm.

B. Corolla:
- *Average diameter.*—48 mm.
- *Form.*—Semi-double; round to asymmetric.
- *Color (general tonality from a distance of three meters).*—Red. Upper Surface: 44A.

C. Bud:
- *Shape.*—Round to oval. Flat top.
- *Color.*—Red; slightly marbled.

D. Reproductive organs:
- *Androecium.*—6–8 stamens.
- *Gynoecium.*—5–6 lobed stigma.

E. Spring flowering response period: In Hillscheid, Federal Republic of Germany, in 1983, 40% of plants opened with at least one flower 13 weeks after planting of unrooted cuttings.

F. Outdoor flower production: The total flower count in 1983 in Hillscheid, Federal Republic of Germany, was between 35 and 38 flowers per plant for the June through October observation period.

G. Durability: Very good.

PLANT

A. Foliage:
- *Form.*—Kidney shaped.
- *Margin.*—Generally rounded, crenate.

*Color.*—Top surface: Very dark green, 136A-B.
Zonation: Weak zonation.
*Tolerance of botrytis.*—Good.

B. General appearance and form:
*Internode length.*—29 mm.
*Branching pattern.*—2.8 branches per plant.
*Height.*—270 mm.

I claim:

1. A new and distinct cultivar of geranium named Tango, as described and illustrated, and particularly characterized by its red flower color; semi-double flower form with large flowerhead; dark green foliage; fast rooting; very good chlorophyll quality for transportation; small zonation; and good weather resistance.

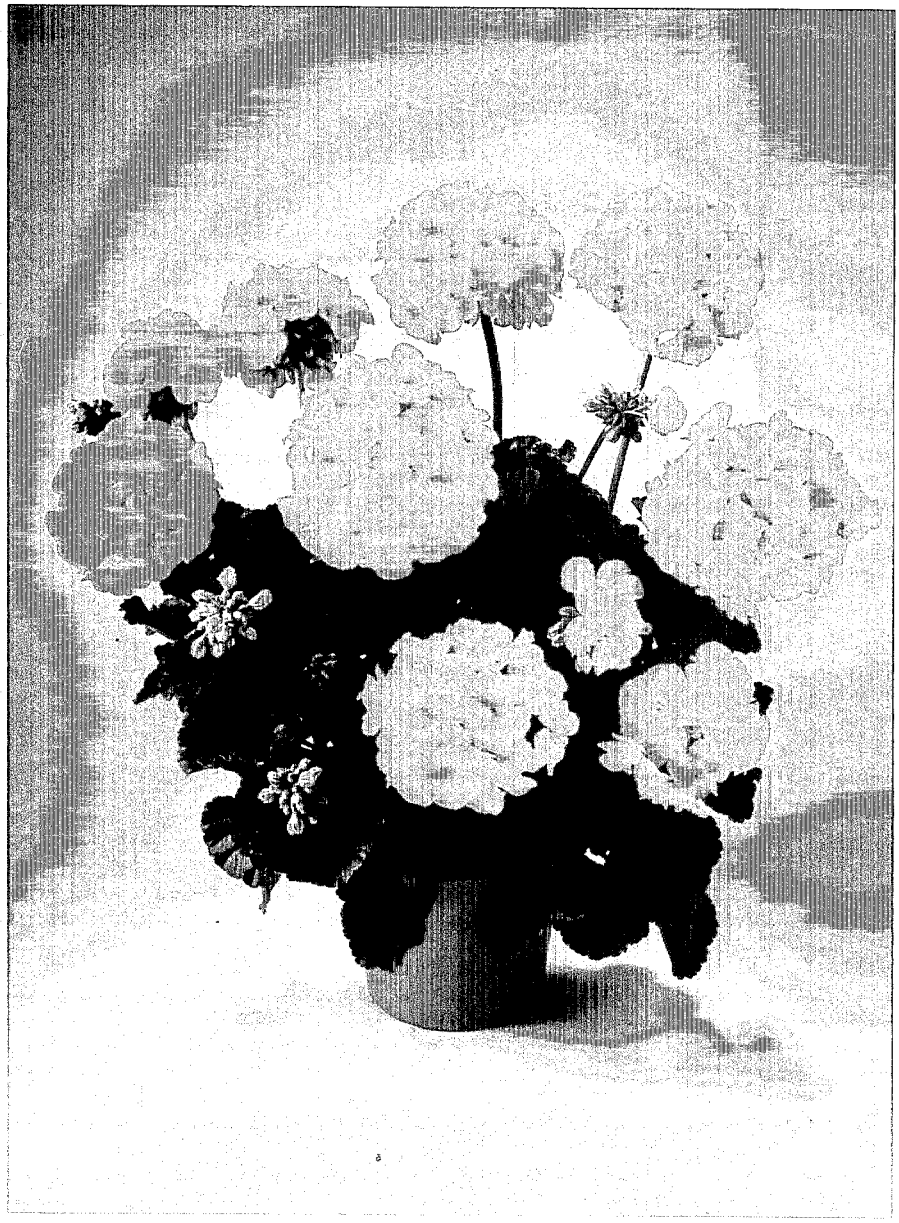

* * * * *